United States Patent [19]
Montague et al.

[11] Patent Number: 5,688,272
[45] Date of Patent: Nov. 18, 1997

[54] TOP-TIGHTENING TRANSVERSE CONNECTOR FOR A SPINAL FIXATION SYSTEM

[75] Inventors: Leslie A. Montague, Cordova; Michael C. Sherman, Memphis; Eddie Ray, III, Cordova, all of Tenn.

[73] Assignee: Danek Medical, Inc., Memphis, Tenn.

[21] Appl. No.: 413,387

[22] Filed: Mar. 30, 1995

[51] Int. Cl.$^6$ .................................................. A61B 17/70
[52] U.S. Cl. ............................................... 606/61; 606/72
[58] Field of Search ............................ 606/61, 60, 69, 606/70, 71, 72, 73

[56] References Cited

U.S. PATENT DOCUMENTS

| | | |
|---|---|---|
| 4,655,199 | 4/1987 | Steffee . |
| 4,743,260 | 5/1988 | Burton . |
| 4,815,453 | 3/1989 | Cotrel . |
| 4,950,269 | 8/1990 | Gaines, Jr. . |
| 4,987,892 | 1/1991 | Krag et al. . |
| 5,005,562 | 4/1991 | Cotrel . |
| 5,024,213 | 6/1991 | Asher et al. . |
| 5,053,034 | 10/1991 | Olerud . |
| 5,084,049 | 1/1992 | Asher et al. ............................ 606/61 |
| 5,122,131 | 6/1992 | Tsou . |
| 5,147,360 | 9/1992 | Dubousset . |
| 5,176,678 | 1/1993 | Tsou . |
| 5,181,917 | 1/1993 | Rogozinski ............................ 606/61 |
| 5,209,752 | 5/1993 | Ashman et al. . |
| 5,246,442 | 9/1993 | Ashman et al. . |
| 5,261,909 | 11/1993 | Sutterlin et al. . |
| 5,282,801 | 2/1994 | Sherman . |
| 5,312,405 | 5/1994 | Korotko et al. ....................... 606/61 |
| 5,334,203 | 8/1994 | Wagner ................................. 606/61 |
| 5,413,602 | 5/1995 | Metz-Stravenhagen .............. 623/17 |

FOREIGN PATENT DOCUMENTS

| | | | |
|---|---|---|---|
| 536066 | 4/1993 | European Pat. Off. ............... | 606/61 |

OTHER PUBLICATIONS

"TSRH$^R$ Surgical Technique Manual": by Danek Medical, Inc., published in 1990.

"Universal Instrumentation (CD) for Spinal Surgery" by Stuart. pp. 1–15.

"ISOLA™ Transverse Rod Connectors" brochure by AcroMed Corporation.

"Spinal Internal Fixator" manual by Synthes. Date Unknown, 23 page.

*Primary Examiner*—Guy V. Tucker
*Attorney, Agent, or Firm*—Woodard, Emhardt, Naughton, Moriarity & McNett

[57] ABSTRACT

A new top-loading transverse connector of the present invention for bridging between longitudinal members of a spinal fixation system implant. The transverse connector is loaded and clamped to the longitudinal member from the top permitting easy access and adjustment and may clamp at the same location along the rod as a vertebral fixation element. The transverse connector comprises an elongate body and an engagement portion on each opposing end of the elongate body. The engagement portion includes downward legs each with a surface to engage the longitudinal member. The downward legs are displaced from each other to define a space therebetween. The engagement portion includes an upper surface defining an opening therethrough. The opening intersects the space defined between the downward legs. Together, the space and opening are configured to receive the clamp assembly carried on the longitudinal member. Another object of the invention, is to provide an improved system including the transverse connector. Another object of the invention is to provide a transverse connector that clamps to the longitudinal member at a variable angle. Another object of the invention is to provide a separate engagement portion which can be used with existing transverse connectors to permit clamping at the same site as vertebral fixation elements. Another object of the invention is to provide a way to adjust the length of the elongate body of the transverse connector.

26 Claims, 8 Drawing Sheets

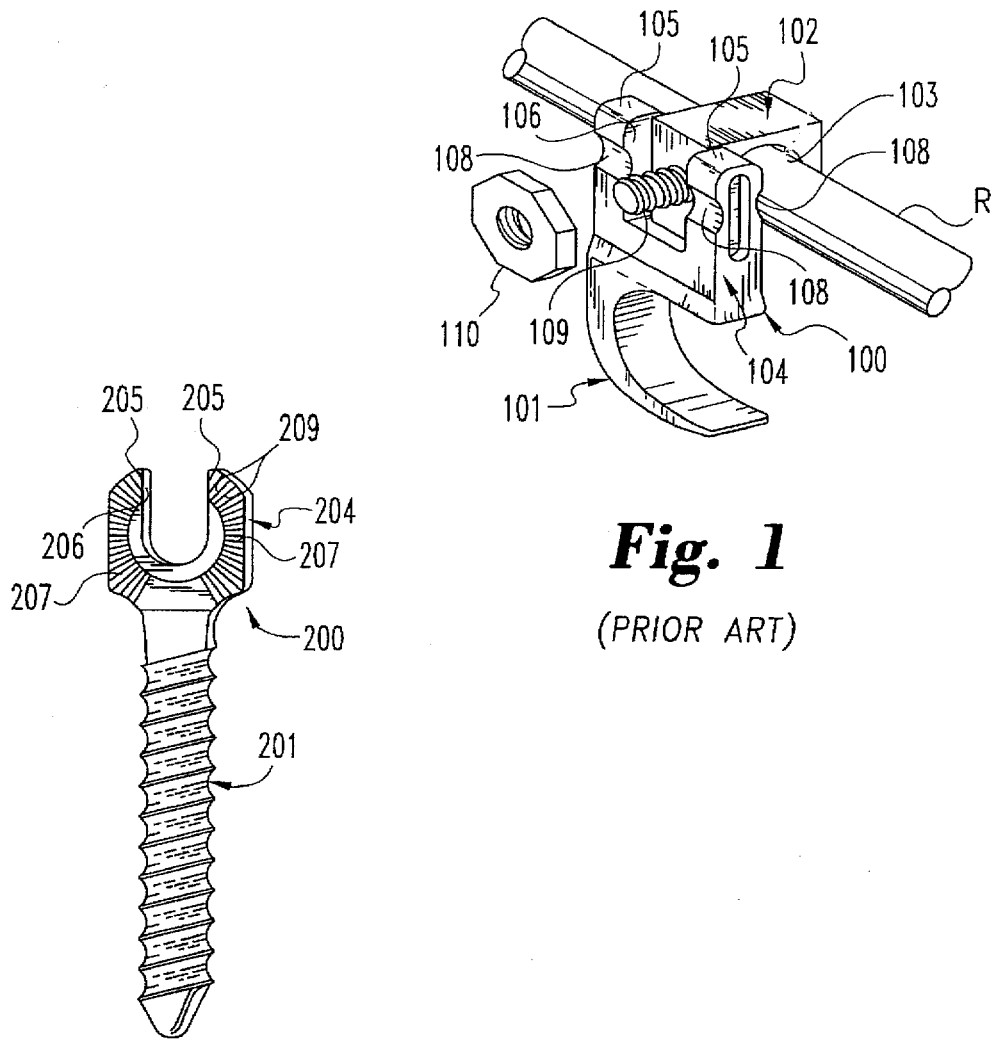
Fig. 1
(PRIOR ART)
Fig. 2
(PRIOR ART)
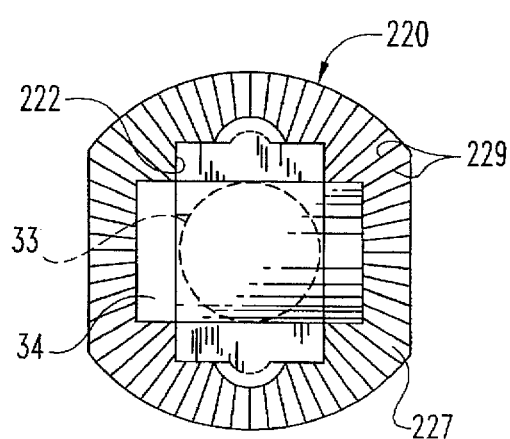
Fig. 3
(PRIOR ART)

TOP-TIGHTENING TRANSVERSE CONNECTOR FOR A SPINAL FIXATION SYSTEM

BACKGROUND OF THE INVENTION

The present invention concerns spinal fixation systems, and particularly systems utilizing elongated rods adjacent to the spinal column. More specifically, the invention concerns improvements to a device which connects two approximately parallel elongate members, such as spinal rods, to enhance rigidity of the system.

Spinal fixation systems are implanted during a surgical procedure to treat a variety of problems. These treatments include correction of congenital spinal deformities, repair of spinal injuries and fusion of vertebra to stabilize degenerative conditions and alleviate chronic lower back pain. Several techniques and systems have been developed for correcting and stabilizing the spine and facilitating spinal fusion. In one common system, a longitudinal member, such as a bendable rod, is disposed along the vertebral column and is fixed to various vertebrae along the length of the column by way of a number of fixation elements. A variety of these vertebral fixation elements can be provided, such as hooks or bone screws, which are configured to engage specific portions of the vertebra. Usually, the surgeon first attaches the vertebral fixation elements to the spine in appropriate anatomic positions, and then attaches each vertebral fixation element to the spinal rod.

Commonly, two or more rods each with a number of vertebral fixation elements are used. Typically, two nearly parallel rods are employed, one on each side of the spinous processes of the vertebral column. The TSRH® Spinal System sold by Danek Medical, Inc. is often configured in this manner. Details of the TSRH® Spinal Implant System are disclosed in the "TSRH® Surgical Technique Manual" provided by Danek Medical, Inc., published in 1990, which disclosure is incorporated herein by reference.

Existing vertebral fixation element attachment means include attachment to a clamp body which clamps on a longitudinal member with the attachment means operating independently of clamping the clamp body to the longitudinal member. Examples of such a system are shown in U.S. Pat. Nos. 5,024,213 and 4,987,892. Similarly, a clamp body for clamping to a longitudinal member may be integrally formed as part of the vertebral fixation element as disclosed in U.S. Pat. Nos. 5,147,360, 5,005,562 and 4,950,269. Numerous other methods of attaching a vertebral fixation element to a clamp body which, in turn, is clamped to a longitudinal member are known to those of ordinary skill in the art.

One improvement known in the art is to attach the vertebral fixation element by way of clamping to the longitudinal member. For example, the TSRH® Spinal System clamps the vertebral fixation elements to the rod by way of eyebolts. The eyebolts are positioned on the spinal rod and captured within yolks of the vertebral fixation elements. Specifically, FIG. 1 depicts an existing system described in U.S. Pat. No. 5,246,442 to Ashman et al. for clamping a spinal hook 100 to rod R. Eyebolt 102 is threaded on to rod R by inserting rod R through passage 103. Spinal hook 100 has a vertebra engaging portion 101 and a connection portion 104 extending from the vertebra engaging portion 101. The connection portion 104 is formed by a pair of posts 105 which define a slot 106 therebetween. Also, the posts 105 have opposing lateral surfaces 108 in the form of grooves for engaging rod R. Slot 106 is configured to receive threaded stem 109 formed on eyebolt 102. Nut 110 is configured to engage the threaded stem 109. The hook 100 is clamped to rod R by threading the nut 110 on threaded stem 109 received in slot 106 so that the nut 110 presses against the hook 100 disposed between the threaded nut 110 and the rod R. This assembly offers a 3-point shear clamp of high structural integrity.

A system disclosed in U.S. Pat. No. 5,261,909 to Sutterlin et al., includes a variable angle bone screw clamped to rod R using an eyebolt, as depicted in FIG. 2. In particular, variable angle bone screw 200 has a vertebral engaging portion 201 and a connection portion 204 extending from the vertebral engaging portion 201. The connection portion 204 is formed by a pair of posts 205 which define a slot 206 therebetween for receiving a clamping means such as an eyebolt stem. Also, the posts 205 have opposing lateral surfaces, with the preferred configuration of these surfaces including at least one opposing lateral surface 207 having a plurality of radial splines 209.

Referring to FIG. 3, a clamp assembly washer 220 is shown for use in engaging the variable angle screw 200. The Clamp assembly washer 220 has an opening 222 for passing over bar 34 with projection 33 extending therethrough. The mating surface 227 of the clamp assembly washer 220 includes a plurality of radial splines 229 for interdigitating engagement with the radial splines 209 of the splined surface 207 of the variable angle bone screw 200 shown in FIG. 2. The interdigitation of the washer splines 229 and the bone screw splines 209 facilitate rigid fixation of the variable angle bone screw 200 at non-vertical angles in relation to an attached clamp assembly when the splined surface 207 and the mating surface 227 are clamped together. Further details of this assembly are disclosed in U.S. Pat. No. 5,282,801.

Notably, some clamping assemblies require extensive access to the side of the assembly. Because surgical access is ordinarily from the posterior of the patient, this "side tightening" presents some difficulties. Specifically, the threaded stem of the eyebolt and the nut engaging the stem both project laterally away from the rod. It has been found in practice that it is often cumbersome to engage the nut with a wrench to tighten the nut onto the eyebolt assembly. Moreover, simple mechanics dictates that the wrench can only be moved through a partial turn before the handle of the wrench contacts the surrounding tissue. This necessitates taking the wrench off of the nut and re-engaging it for an additional partial rotation. Ratchet-type wrench systems are typically not acceptable in procedures of this sort because the lateral space required for the ratchet mechanism unnecessarily impinges on the surrounding tissue and requires greater space at the surgical site. Consequently, a subsequent improvement is disclosed in the U.S. Pat. No. 5,282,801 to Sherman. This improvement clamps a vertebral fixation element and rod together by way of a 3-point shear clamp assembly. Notably, this assembly is "top-tightening" because a set screw, completely accessible from the top, is used to initiate and adjust the clamping of the components.

It is a primary goal of the surgeon using a spinal implant system to obtain maximum construct rigidity. Thus, once two rods are fixed to various vertebral fixation elements along the spine, each on opposing sides of the spinous processes, a rigid transverse connection which bridges the rods is often desired. This transverse connection improves overall spinal fixation system integrity. One method used is an adjustable transverse rod to connect the two main rods as shown in U.S. Pat. No. 5,005,562 to Cotrel. One problem with this approach is that the transverse connector clamp is separate from the vertebral fixation element clamps. As a result, the transverse connector requires additional space along the length of the rod limiting the configurations possible with respect to the vertebral fixation element clamps. Also, the relative size and bulkiness of this transverse connection method complicates implantation and limits the connection options available to the surgeon. The size and bulkiness of the system is especially important because a significant portion of the patient population for spinal implant fixation systems is made up of pediatric patients. Bulky implants are not easily implanted into small, thin people because the space around the vertebra is limited. Also, in patients with severe deformities of the spinal column, the vertebral fixation sites are often severely limited, so connection flexibility is paramount. Finally, the transverse rod does not provide exclusive top-tightening ability complimentary to recent vertebral fixation element clamping improvements.

Similarly, the "TSRH® Surgical Manual", illustrates a rigid transverse bar or CROSSLINK® connecting the rods by way of eyebolt clamps. Similar to the vertebral fixation element attachment, an eyebolt is strung on each rod prior to clamping. The transverse connector receives the threaded stem of the eyebolt through an opening on opposing ends of the connector. A nut is then threaded on each stem to clamp the transverse connector between the nut and the rod at each opposing end. Although this assembly permits top-tightening at the associated clamp, it requires anticipating the placement of additional dedicated eyebolts prior to clamping the vertebral fixation elements to the rod. Also, it still suffers from the size, bulkiness and "rod crowding" constraints of other systems because it does not facilitate clamping at the same site as a vertebral fixation element.

Spinal procedures are rapidly becoming prevalent surgeries, largely because of the high incidence of low back pain. In the past, surgical techniques for alleviating low back pain or for addressing deformities or injuries has required fairly complicated and massive surgical procedures. The focus in recent times has been to greatly reduce the degree of invasion into the patient required for stabilizing a spine with instrumentation, as well as to reduce the amount of trauma to tissue surrounding the instrumentation, both during the procedure and after the spinal instrumentation has been implemented. Moreover, an implant which is easy to assemble, simple to adjust and high in rigidity substantially reduces the risk of complications adversely affecting a patient.

Consequently, there is a need for a new transverse connector which can connect at the same clamp location along the rod as any vertebral fixation element and still provide the rigidity of existing connectors, preferably offering the integrity of a 3-point shear clamp configuration. Furthermore, this new connector needs to clamp directly to the rod and be removable without disassembly of vertebral fixation elements clamped to the rod. A top-loaded device harmonizes these goals. Also, this new connector would ideally offer a clamping mechanism which is installed and adjusted independent of the vertebral fixation element clamping. Finally, the ease of adjustment inherent in a top-tightened system should be available for the transverse connector clamp, while preserving top-tightening clamp adjustment for the vertebral fixation elements.

SUMMARY OF THE INVENTION

A new transverse connector for bridging between longitudinal members of a spinal fixation system is provided by the present invention which is top-loaded and top-tightening. The transverse connector clamps at the same location along the longitudinal member of a spinal fixation system as a vertebral fixation element thereby reducing crowding along the longitudinal member. Also, the transverse connector of the present invention offers 3-point clamping capability to assure rigid connection of the longitudinal members. More particularly, in one aspect of the invention, the transverse connector comprises an elongate body defining a longitudinal axis along its length for spanning the transverse distance between two longitudinal members. The elongate body includes opposing ends, each with an engagement portion. The engagement portion has a pair of downward legs displaced from each other to define a space therebetween. Each leg has a lower surface configured to engage a longitudinal member. Each lower surface of each leg is coplanar to the other. The engagement portion has an upper surface in the plane of the longitudinal axis of the elongate body. This upper surface defines an opening therethrough. The opening intersects the space defined between the pair of legs. The space and opening are configured to receive the clamp assembly therein when the transverse connector is disposed between the two longitudinal members. When clamped to a longitudinal member the axis along the length of the elongate body is generally perpendicular to the axis along the length of the longitudinal member.

Another object of the present invention is to provide an improved system including the transverse connector. This system includes a fastener for fastening the transverse connector to the longitudinal member. For example, one system includes a clamp assembly providing a single means of clamping the transverse connector and a vertebral fixation element to a longitudinal member. Alternatively, another system provides a means of attaching or clamping the vertebral fixation element which is independent of the means for clamping the transverse connector to the longitudinal member. Another aspect of the improved system is that it fastens or clamps the transverse connector at the same location along the longitudinal member as the means for vertebral fixation element clamping or attachment.

Another embodiment of the invention provides a top-loading variable angle transverse connector for bridging between two longitudinal members extending adjacent the spine of a patient, and each carrying a clamp assembly thereon. This embodiment permits clamping of the transverse connector at various angles between the axis along the length of the elongate body and the axis along the length of the longitudinal member. As a result, this embodiment bridges longitudinal members with less restriction on the relative location of the clamp assemblies on each longitudinal member used to clamp the transverse connector. Specifically, this embodiment comprises an elongate body defining a longitudinal axis along its length for spanning the transverse distance between said two longitudinal members. Opposite ends of the elongate body each include an engagement portion. Each engagement portion has a contact portion integrally formed on each opposing end of said elongate body. The contact portion has an upper surface and an opposing clamping surface. These opposing surfaces define a contact portion opening therethrough. The walls of this contact portion opening define a groove therein. Also, each engagement portion has an engagement washer with a pair of downward legs displaced from each other to define a space therebetween. Each of these legs includes a lower surface configured to engage the longitudinal member. The lower surfaces of each of these legs are coplanar to each other. The engagement washer has a mating surface configured to engage the clamping surface of the contact portion and defining an engagement washer opening therethrough. The engagement washer opening intersects the space defined between the pair of legs. The engagement washer has a plurality of interlocking tabs extending vertically from the mating surface for engaging the groove of the contact portion and aligning the contact portion opening with the engagement washer opening. As a result, the space, the contact portion opening and the engagement washer opening are configured to receive a clamp assembly therein when the variable angle transverse connector is disposed between two longitudinal members and the engagement washer is coupled to the contact portion on each opposing end of the elongate body.

Another aspect of the present invention includes an engagement washer for clamping an existing transverse connector to a longitudinal member at the same location as a vertebral fixation element. This embodiment permits top-loading and top-tightening of an existing transverse connector. The engagement washer includes a pair of downward legs displaced from each other to define a space therebetween. Each of the legs includes a lower surface configured to engage the longitudinal member. The lower surface of each of leg is coplanar to the other. The engagement washer includes a mating surface configured to clamp to an existing transverse connector. Also, the mating surface defines an engagement washer opening therethrough. The engagement washer opening intersects the space defined between the pair of legs. As a result, the space and engagement washer opening are configured to receive a clamp assembly therein when the existing transverse connector is clamped to the mating surface.

Another variation of the present invention is the ability to vary the length of the elongate body. In this variation, the elongate body is formed from two arms. A first arm with a first end and a second arm with a second end. A joining clamp connects the first arm to the second arm so that the first end is opposite the second end. The arms are approximately parallel to the longitudinal axis of the elongate body when connected. The joining clamp is adjustable to fix the length between the first and second ends and each end includes an engagement portion. One configuration of the joining clamp includes a joining clamp body integrally attached to the second arm which defines a passage for receiving the first arm. This passage is approximately parallel to an axis along the second arm. A threaded bore intersects the passage which is configured for engagement by a set screw with a tip to bear against the first arm. Similarly, instead of integral attachment to the joining clamp body, the second arm may be adjustably clamped to the joining clamp body like the first arm. Alternatively, the first arm has a joining clamp body defining a nesting passage along a portion of the length of the first arm. The second arm has a nesting portion on its joining end configured to nest within the nesting passage. The joining clamp includes a threaded bore through the outer wall of the first arm which intersects the nesting passage. The threaded bore is configured for engagement by a set screw having a tip configured to engage the second arm nesting within the nesting passage.

Related objects and advantages of the present invention will be apparent from the following description.

BRIEF DESCRIPTION OF THE DRAWINGS

FIG. 1 is a perspective view of a spinal hook of the prior art engaged on a spinal rod by way of an eyebolt assembly.

FIG. 2 is a variable angle bone screw of the prior art for use in a top-tightening clamp assembly depicted in FIGS. 6–10.

FIG. 3 is a side elevational view of a washer of the prior art disposed on the clamp assembly shown in FIGS. 6–10.

DESCRIPTION OF THE PREFERRED EMBODIMENT

Figure 4:
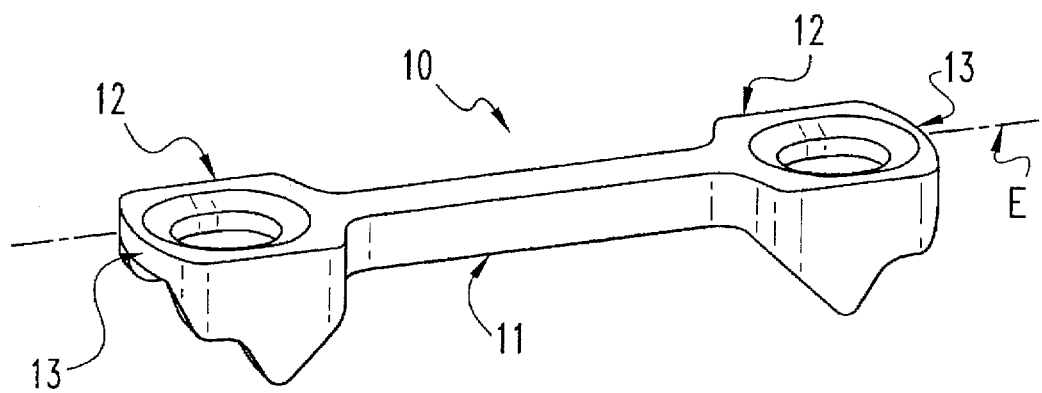
FIG. 4 is a perspective view of a transverse connector in accordance with one embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 4, a top-loading transverse connector 10 is illustrated which is configured for bridging between two longitudinal members each extending adjacent the spine of a patient and carrying a clamp assembly thereon. The transverse connector 10 is preferably formed from medical grade stainless steel, titanium, titanium alloy, or other biocompatible material. In the preferred embodiment, transverse connector 10 includes an elongate body 11 defining a longitudinal axis E along its length for spanning the transverse distance between longitudinal members. In the preferred embodiment of the transverse connector 10, elongate body 11 includes an engagement portion 12 integrally formed on each opposing end 13. Alternatively, engagement portion 12 may be formed at various other locations along elongate body 11.

Figure 5:
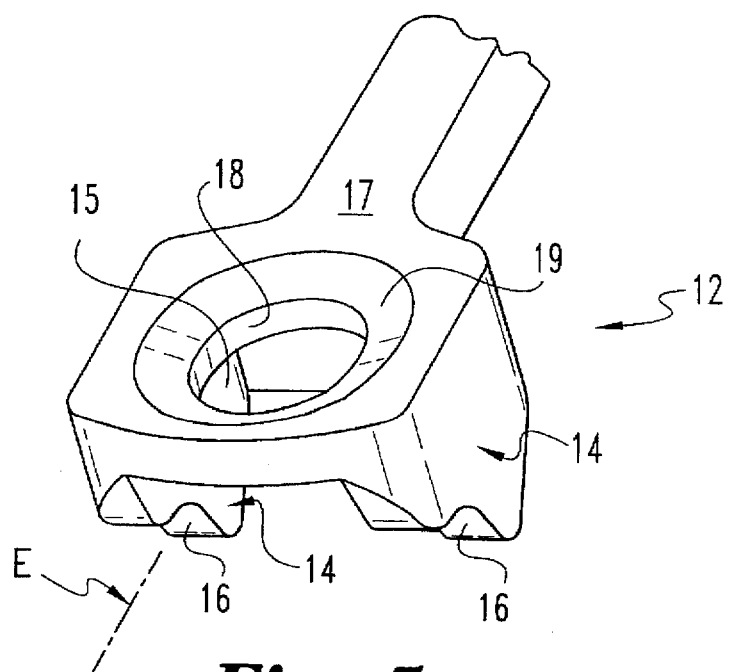
FIG. 5 is a perspective view of an engagement portion of the transverse connector shown in FIG. 4.

To enhance clarity, FIG. 5 depicts only one engagement portion 12, but it should be understood that the preferred embodiment of the transverse connector 10 includes an engagement portion 12 on each opposing end 13. Now referring to FIG. 5, engagement portion 12 includes a pair of downward legs 14 which are displaced from each other generally perpendicular to axis E. As a result of this displacement, the downward legs 14 define a space 15 between the downward legs 14. Each downward leg 14 includes a lower surface 16 configured so the lower surfaces 16 are coplanar to each other. Preferably, the transverse connector 10 is symmetric about a plane coincident with axis E and between downward legs 14 of each engagement portion 12, and is also symmetric about a plane formed perpendicular to the axis E and between the engagement portions 12. This symmetry makes the engagement portions 12 interchangeable.

The upper surface 17, in a plane of axis E, defines an opening 18 therethrough and intersecting the space 15. Opening 18 is preferably an elongate bore or slot with a major axis generally parallel to the axis E. Alternatively, the opening 15 could be a circular bore or a slot open on the end 13. Also, upper surface 17 defines a recess 19 bordering the opening 18. In other embodiments, the recess 19 may be absent.

Figure 6:
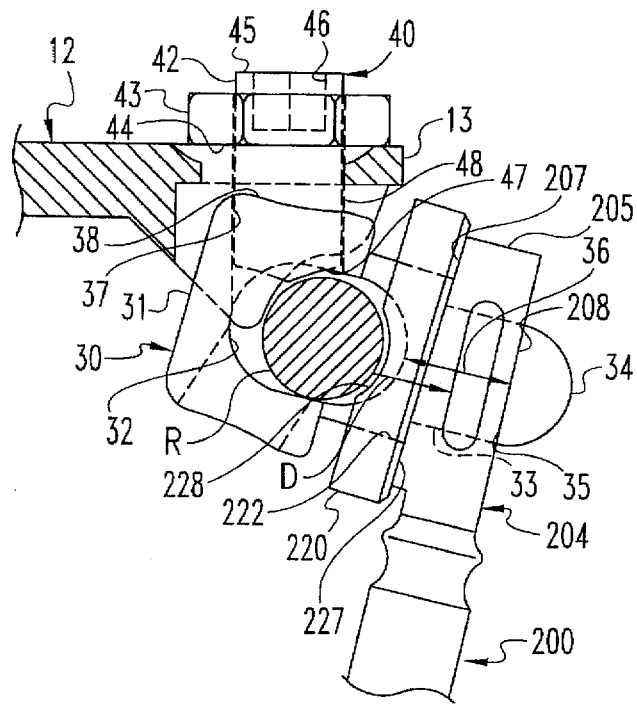
FIG. 6 is an end elevational, partial cross-sectional, view of a top-tightening clamp assembly for clamping an engagement portion in accordance with one embodiment of the present invention.

Now referring to FIG. 6, the orientation of engagement portion 12 of the transverse connector 10 with respect to a clamp assembly 30 is depicted. The space 15 and opening 18 receive at least a portion of clamp assembly 30. The clamp assembly 30 includes a clamp body 31 which defines a passage 32 therethrough for receiving rod R. The downward legs 14 straddle the clamp assembly 30 when the lower surfaces 16 engage the rod R received in passage 32. Because FIG. 6 provides a partial cross-sectional view, only one downward leg 14 with a lower surface 16 is shown on the far side of the clamp assembly 30, but it should be understood that the downward leg 14 with a lower surface 16 not shown is similarly disposed on the near side of clamp assembly 30. Refer to U.S. Pat. No. 5,282,801 for details concerning the construction of clamp assembly 30, which details are incorporated herein by reference.

Each lower surface 16 is configured to engage a generally cylindrical longitudinal member presenting a circular cross-section, such as rod R, but the lower surfaces 16 may be configured to engage a variety of cross-sectional shapes presented by a longitudinal member. When the lower surfaces 16 engage the longitudinal member, the axis E is generally perpendicular to the axis along the length of the longitudinal member. Preferably, lower surfaces 16 define a cam surface to outwardly displace a longitudinal member when engaged by lower surfaces 16. The "outward" direction in this context is away from the end 13 of the engagement portion 12 and toward the rod R received in passage 32. As shown in FIG. 6, the lower surfaces 16 are formed with a curved shoulder to outwardly cam rod R in the direction D.

In the present invention, a fastener is envisioned for connecting each engagement portion 12 to a longitudinal member. Preferably, this fastener is part of a clamping means for clamping the transverse connector 10 to the longitudinal member. Furthermore, in order to minimize crowding by various clamping structures, at least one of these transverse connector fasteners employs the same structure as the means for attaching the connection portion of a vertebral fixation element to the longitudinal member. In one preferred embodiment, the vertebral fixation element attachment means is a clamping means for clamping the connection portion of the vertebral fixation element directly to the longitudinal member. In a variation of this embodiment, the connection portion is indirectly clamped to the longitudinal member because one or more additional elements are concurrently clamped between the longitudinal member and the connection portion- In either case, the transverse connector clamping means and vertebral fixation element clamping means are independently adjustable and provide top-tightening for both clamping means. The top-tightening vertebral fixation element clamp assembly in U.S. Pat. No. 5,282,801 discloses details concerning vertebral fixation element clamping means similar to the present invention. Likewise, U.S. Pat. Nos. 5,261,909 and 5,246,442 disclose vertebral fixation elements preferred for use with the present invention. Consequently, U.S. Pat. Nos. 5,282,801, 5,261,909 and 5,246,442 are incorporated by reference herein. Various aspects of these patents important to the novel features of the present invention are duplicated in the following disclosure as necessary.

Figure 7:
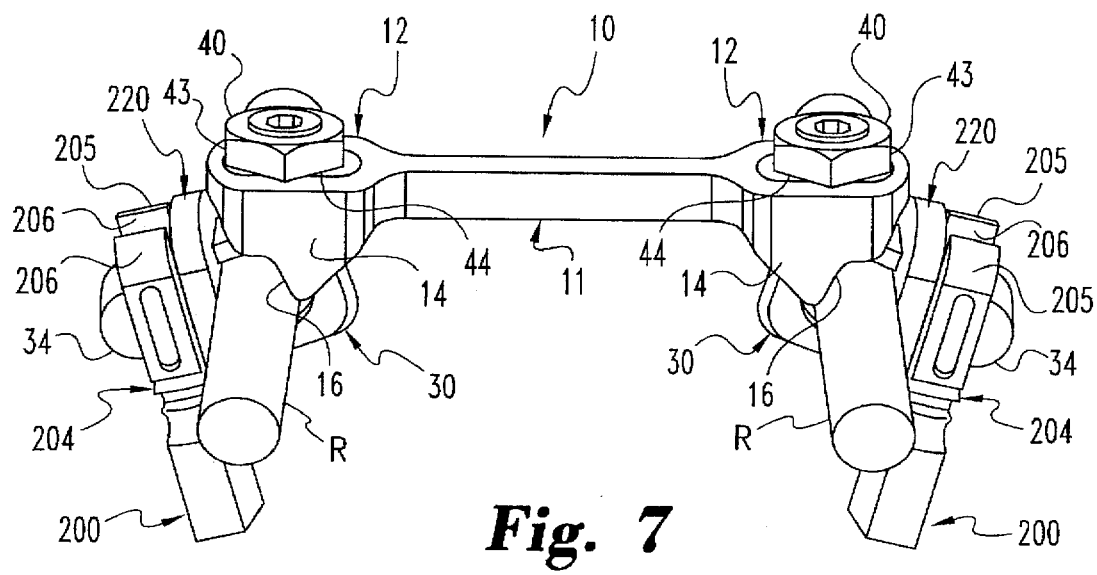
FIG. 7 is a perspective view of the transverse connector shown in FIG. 4 with the engagement portion on each opposing end clamped to a rod by the assembly shown in FIG. 6.

A top-loaded transverse connector with a top-tightened clamping means using the same clamping structure as a top-tightened vertebral fixation element clamping means is accomplished using the clamp assembly 30 shown in FIGS. 6 and 7. Referring specifically to FIG. 6, the clamp assembly 30 includes a projection 33 which is integrally formed on the clamp body 31 extending generally perpendicular to the longitudinal axis of rod R received in 32. The projection 33 terminates in a bar 34 which includes an inward surface 35. Reference to the "inward" direction in connection with clamp assembly 30 is intended to mean facing toward rod R received in the passage 32. In this preferred embodiment, the bar 34 is arranged as a T-bar, so named because the bar 34 combined with the projection 33 are in the shape of a "T" with the T-bar arranged generally parallel to the longitudinal axis of rod R extending through the passage 32.

The passage 32 is an elongated bore so that rod R can at least initially move along the longitudinal axis of the passage 32 transverse to the longitudinal axis of the rod R received therein. The clamp assembly 30 is particularly designed so the distance between the inward surface 35 and the closest point of the passage 32, as indicated by distance 36, is less than the cumulative width of the element or elements to be clamped between the inward surface 35 and the rod R received in the passage 32.

The clamp body 31 has a top surface 38 which defines a threaded bore 37 intersecting passage 32. The threaded bore 37 is adapted to receive a set screw 40 therein. Set screw 40 includes a threaded stem 48 having threads for mating with bore 37. Moreover, set screw 40 has a threaded proximal end 42 configured for engagement by a nut 43 with a bottom surface 44. The top surface 45 of the threaded proximal end 42 defines a cavity 46 to accommodate an instrument to torque the set screw 40 such as an Allen head wrench. Alternatively, the shape of cavity 46 can be altered to accommodate various other torquing instruments such as a Phillips or flat blade screwdriver. The distal end of the threaded stem 48 is a tip 47 configured to engage rod R. Preferably, the tip 47 is formed in a spherically conical shape, to provide a line contact with the rod R along the curvature of the tip. Alternatively, the tip 47 may also be rounded or blunt, thereby providing essentially a point contact with the spinal rod. With the spherically conical shape tip 47, it is preferred the threaded bore 37 intersect the passage 32 at a non-perpendicular angle to the longitudinal axis of the bore. This angle should allow a firm contact between the tip 47 of the set screw 40 and the rod R, while also keeping the threaded proximal end 42 accessible from the top of the implanted construct.

As can be seen more clearly in FIG. 7, the slot 206 of the connection portion 204 receives the projection 33 between the posts 205 of the variable angle bone screw 200. Returning to FIG. 6, the connection portion 204 of the variable angle bone screw 200 is disposed between the inward surface 35 of the bar 34 and a clamp assembly washer 220. The opposing lateral surfaces of the posts 205 are the splined surface 207 which is adjacent the mating surface 227 of the clamp assembly washer 220 and the contact surface 208 which is adjacent the inward surface 35.

Similarly, clamp assembly washer 220 has an opening 222 so that it can pass over the bar 34 and the projection 43 can extend therethrough as shown. Clamp assembly washer 220 has opposing lateral surfaces including the clamping surface 228 configured to engage rod R, and the mating surface 227 for mating with the splined surface 207 of the connection portion 204 of the variable angle bone screw 200.

With the foregoing description of the transverse connector 10 in FIGS. 4 and 5, and the clamp assembly 30 in FIG. 6, the manner of assembling the spinal fixation system with a transverse connector 10 for this preferred embodiment is provided so that it may be clear to one of ordinary skill in the art. First, on each side of the spinous processes, a fixation system comprising a rod R is assembled using a plurality of vertebral fixation elements. Specifically, a surgeon engages each vertebral fixation element with the vertebra in an anatomically suitable location. The rod R is then positioned appropriately to provide for clamping of the vertebral fixation element. Alternatively, rod R can already be positioned rigidly at its ends or at various locations along rod R. In this instance, an additional vertebral fixation element could be added subsequent to positioning of the rod R and the clamp assembly 30 would be used to engage the vertebral fixation element to rod R. The set screw 40 is initially loosely threaded into the bore 37 so that there is adequate free play between the rod R and the walls of the passage 32. In addition, the clamp assembly 30 is permitted to slide along the length of rod R to the desired location of the vertebral fixation element.

Once the clamp assembly is positioned adjacent to a vertebral fixation element connecting portion 204, the projection 33 is received in the slot 206 through the posts 205. The connection portion is positioned between the clamp assembly washer 220 and the bar 34. Clamp assembly washer 220 is preferably slidably engaged on the clamp assembly 30 with the projection 33 extending through opening 222 prior to use as detailed in U.S. Pat. No. 5,282,801.

Next, the set screw 40 is tightened within threaded bore 37 so that the tip 47 contacts the longitudinal member 30 and presses the rod R against the clamping surface 228. In turn, the clamp assembly washer 220 presses against the connection portion 204 which is then pressed against the inward surface 35 of the bar 34. In this way the rod R is clamped between the tip 47 and the clamp assembly washer 220, clamp assembly washer 220 is clamped between the rod R and the variable angle bone screw 200, and the variable angle bone screw 200 is clamped between the clamp assembly washer 220 and the bar 34. The set screw 40 is threaded into the bore 37 as far as possible, finger tight. It has been found that this technique provides adequate clamping of a vertebral fixation element. It should be noted that the width of clamp assembly washer 220 can vary so that the distance spanned by set screw 40 to the rod R correspondingly varies in order to provide adequate clamping. Similarly, the length of projection 33 may vary so that the distance spanned by the set screw 40 to rod R required to provide adequate clamping correspondingly varies.

To clamp transverse connector 10 to rod R, the engagement portion 12 of one end 13 of the transverse connector 10 is placed over the clamp assembly 30 so that the downward legs 14 straddle the clamp assembly 30 and the lower surfaces 16 engage rod R received in the passage 32. Moreover, the placement provides for the threaded proximal end 42 of the set screw 40 to pass through the opening 18 even when the screw 40 is threaded in the bore 37 to the point of engagement of rod R. Transverse connector 10 is clamped to the rod R by threading the nut 43 so the bottom surface 44 contacts the upper surface 17 of the engagement portion 12. As the nut 43 presses against the upper surface 17 of engagement portion 12, the lower surfaces 16 press against the rod R, clamping the engagement portion 12 between the nut 43 and the rod R. In this way, the vertebral fixation element attachment means is a clamping means which is initiated and adjusted by way of torquing the set screw 40. Together, set screw 40, threaded bore 37 and nut 43 cooperate to provide the fastener used to connect the transverse connector 10 to the longitudinal member. Moreover, clamping of the transverse connector 10 is independently adjustable by way of threading nut 43 on the threaded proximal end 42 of the set screw 40. Furthermore, both the vertebral fixation element and transverse connector clamping means are adjustable via top-tightening.

In its preferred use, a top-loading transverse connector bridges two longitudinal members extending adjacent the spine of a patient with each longitudinal member carrying a clamp assembly. As shown in FIG. 7, the transverse connector engagement portions 12 on each opposing end 13 are clamped to each of two rods R. The two rods R are generally parallel to each other. The elongate body 11 of transverse connector 10 spans the traverse distance between the two rods R. In this instance, a clamp assembly 30 is shown on each rod R clamping a connection portion 204 of a variable angle bone screw 200 and a clamp assembly washer 220 between the rod R and the bar 34. However, it is contemplated that the transverse connector clamping means and the vertebral fixation element attachment means can vary for different engagement portions 12 on the same transverse connector 10.

In another embodiment, a solitary means clamps the transverse connector to the longitudinal member and the longitudinal member to the vertebral fixation element. Like the independent clamping means discussed previously, the set screw 40, threaded bore 37 and nut 43 cooperate to provide the fastener for the transverse connector 10. The clamp assembly 30 shown in FIGS. 6 and 7 integrates this fastener to provide the alternative single clamping means. Referring back to FIG. 6, it is noted that the curved shoulder of lower surfaces 16 directed against the rod R cams rod R against the clamping surface 228 of clamp assembly washer 220. In turn, clamp assembly washer 220 presses against the connection portion 204 which in turn presses against the inward surface 35 of bar 34. As a result, the clamping of the transverse connector 10 between the nut 43 and the rod R, also clamps the clamp assembly washer 220 between the rod R and the connection portion 204, and the connection portion 204 between the clamp assembly washer 220 and the bar 34. Furthermore, it is realized that clamping of the transverse connector 10, rod R, and the connection portion 204 occurs even if the tip 47 of set screw 40 does not contact the rod R. However, the set screw 40 must at least be threaded into the bore 37 so that the threaded proximal end 42 is situated for engagement by nut 43. Therefore, clamp assembly 30 offers an alternative embodiment by way of a single clamping means for clamping the transverse connector 10, longitudinal member and vertebral fixation element together.

Figure 8:
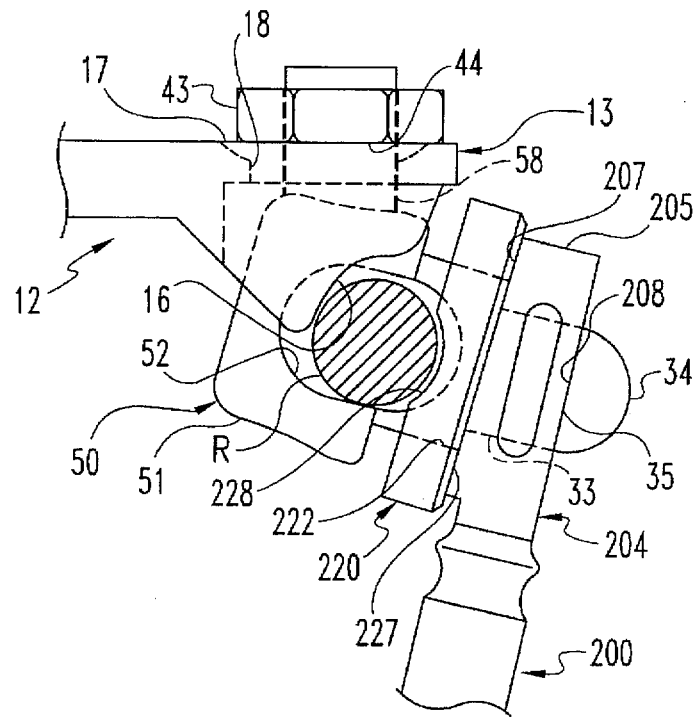
FIG. 8 is an end elevational, partial cross-sectional, view of an alternative top-tightening clamp assembly with a threaded stem and nut to provide a means for clamping the transverse connector to a spinal rod.

Referring to FIG. 8, a less complicated clamp assembly 50 also provides a single clamping means. In this alternative, a threaded stem 58 is integrally attached to the clamp body 51 to serve as a substitute for the threaded proximal end 42 of set screw 40. Similarly, to clamp transverse connector 10 to rod R, the engagement portion 12 of one end 13 of the transverse connector 10 is placed over the clamp assembly 50 so that the downward legs 14 straddle the clamp assembly 50 and the lower surfaces 16 engage rod R received in the passage 52. This placement provides for the threaded stem 58 to pass through the opening 18. Transverse connector 10 is clamped to the rod R by threading the nut 43 so the bottom surface 44 contacts the upper surface 17 of the engagement portion 12. As the nut 43 presses against the upper surface 17 of engagement portion 12, the lower surfaces 16 press against the rod R and the curved shoulder of lower surfaces 16 cam rod R against the clamping surface 228 of clamp assembly washer 220. In turn, clamp assembly washer 220 presses against the connection portion 204 which in turn presses against the inward surface 35 of bar 34. As a result, the clamping of the transverse connector 10 between the nut 43 and the rod R, also clamps the clamp assembly washer 220 between the rod R and the connection portion 204, and the connection portion 204 between the clamp assembly washer 220 and the bar 34. Thus, threaded stem 58 and nut 43 offer a fastener as part of clamp assembly 50 which together provide an alternative single clamping means for clamping the transverse connector 10, longitudinal member and vertebral fixation element together.

Figure 9:
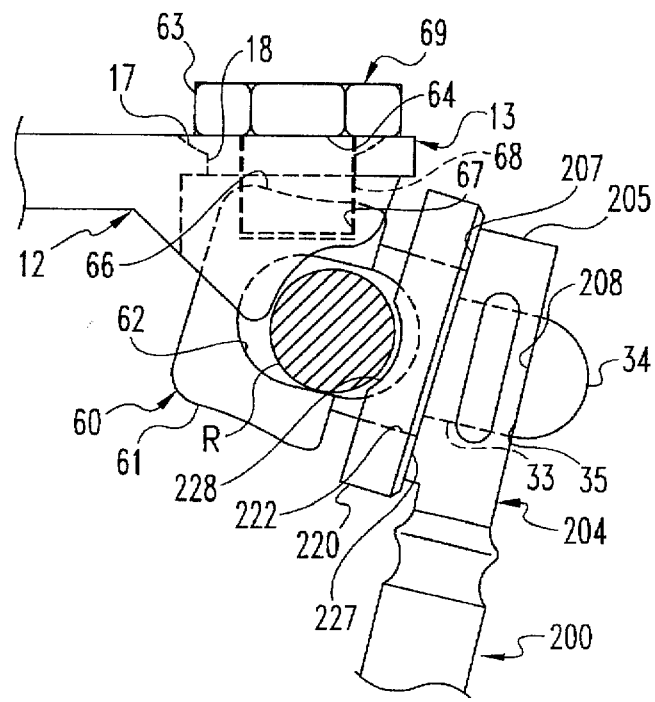
FIG. 9 is an end elevational, partial cross-sectional, view of an alternative top-tightening clamp assembly with a bolt and threaded bore to provide a means for clamping the transverse connector to a spinal rod.

Referring to FIG. 9, clamp assembly 60 provides another single clamping means. In this variation, a bolt 69 is used which has a threaded stem 68 and a bolt head 63 formed on the proximal end. The clamp body 61 has a top surface 66 defining a threaded bore 67 configured to engage the threaded stem 68 of bolt 69. Similarly, to clamp transverse connector 10 to rod R, the engagement portion 12 of one end 13 of the transverse connector 10 is placed over the clamp assembly 60 so that the downward legs 14 straddle the clamp assembly 60 and the lower surfaces 16 engage rod R received in the passage 62. This placement provides for the threaded stem 68 to pass through the opening 18 and engage threaded bore 67. Transverse connector 10 is clamped to the rod R by threading the bolt 69 into threaded bore 67 so that the bottom surface 64 of bolt head 63 contacts the upper surface 17 of the engagement portion 12. As the bolt head 63 presses against the upper surface 17 of engagement portion 12, the lower surfaces 16 press against the rod R, the curved shoulder of lower surfaces 16 cam rod R against the clamping surface 228 of washer 220. In turn, clamp assembly washer 220 presses against the connection portion 204 which in turn presses against the inward surface 35 of bar 34. As a result, the clamping of the transverse connector 10 between the bolt head 63 and the rod R, also clamps the clamp assembly washer 220 between the rod R and the connection portion 204, and connection portion 204 between the clamp assembly washer 220 and the bar 34. Thus, the bolt 69 and threaded bore 67 offer a fastener as part of clamp assembly 60 which together provide an alternative single clamping means for clamping the transverse connector 10, longitudinal member and vertebral fixation element together.

It is noted that the single clamping means offered by clamp assembly 60 shown in FIG. 9, clamp assembly 50 shown in FIG. 8 and alternatively provided by clamp assembly 30 shown in FIG. 6 and 7, all share common structural elements concerning the fastener. First of all, the fastener has a stem attached to the clamp assembly. In particular, this stem is the threaded stem 48 of the set screw 40 in FIGS. 6 and 7, the threaded stem 58 in FIG. 8, and the threaded stem 68 of bolt 69 in FIG. 9. Second, the stem passes through the opening 18 of the engagement portion 12. Although the stem preferably passes through the opening 18, it is envisioned that the stem could be along side the engagement portion 12, as well. In either case, a head is attached to a portion of the stem passing through the opening 18. This head has a bottom surface for adjustably pressing against upper surface 17 of the engagement portion 12. Specifically, this head is a nut 43 in FIGS. 6–8, and a bolt head 63 in FIG. 9. Also, the fastener is adjusted by torquing the threaded elements, but other means of adjustment are envisioned as would occur to those of ordinary skill in the art.

Figure 10:
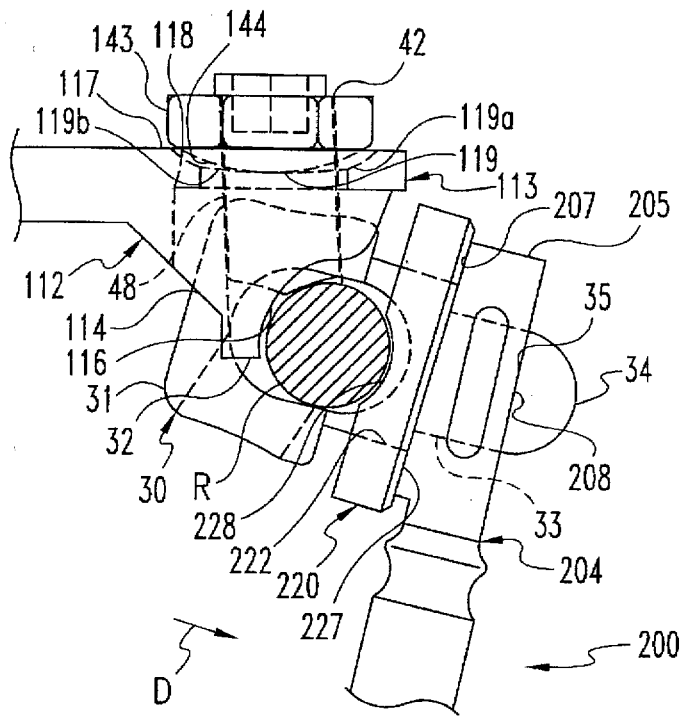
FIG. 10 is an end elevational, partial cross-sectional, view of an alternative to the top-tightening clamp assembly depicted in FIG. 6 with an alternative embodiment of the engagement portion depicted in FIGS. 4 and 5.

Another embodiment replaces the camming action supplied by the curved shoulder of lower surfaces 16 with a sloping recess 119 about the perimeter of opening 118. Referring to FIG. 10, an engagement portion 12 is shown with a recess 119 that slopes from the portion 119a adjacent to the end 113 to inner portion 119b adjacent the elongate body. In other words, this recess 119 slopes away from the portion of opening 118 closest to end 113 toward the portion of the opening 118 farthest way from end 113. This sloped recess 119, or camming surface, is configured to engage a nut 143 specially configured with a spherically shaped bottom surface 144.

To begin clamping of the engagement portion 112, the nut 143 is tightened on the threaded proximal end 42 and the spherical bottom surface 44 initially contacts the slope 119. As the nut 143 is further tightened, the spherical bottom surface 144 slides down the sloped recess 119 until it seats at the inner portion 119b. Consequently, the engagement portion 112 moves toward the rod R as the nut 143 is tightened and the lower surfaces 116 are forced against rod R in the direction D shown in FIG. 10. The motion of the engagement portion 12 presses rod R against the clamping surface 228 of clamp assembly washer 220. In turn, clamp assembly washer 220 presses against the connection portion 204 which in turn presses against the inward surface 35 of bar 34. As a result, the clamping of the transverse connector 10 between the nut 143 and the rod R, also clamps the clamp assembly washer 220 between the rod R and the connection portion 204, and connection portion 204 between the clamp assembly washer 220 and the bar 34.

Thus, the camming offered by the sloped recess 119 in conjunction with the nut 143 having a spherical bottom surface 144 provides an alternative to the curved shoulder of lower surface 16 presented in FIGS. 5–9. As shown in FIG. 10, lower surfaces 116 are configured with a groove for engaging the rod R, but the curved shoulder configuration could also be retained to cam the rod R in concert with the sloped recess 119 and nut 143 having a spherical bottom surface 144. Similarly, the nut 143 participates as part of the transverse connector fastener.

Besides clamping a variable angle bone screw, it is envisioned that other vertebral fixation elements can be clamped using the same clamp assembly as the transverse connector 10. Essentially, these vertebral fixation elements only require a connection portion comparable to connection portion 204 of the bone screw. On the other hand, the clamp assembly washer 220 is not always necessary, so to minimize size and bulkiness of the assembly, another embodiment is envisioned which eliminates clamp assembly washer 220. This embodiment clamps the vertebral fixation element directly to the longitudinal member as shown in FIG. 11.

Figure 11:
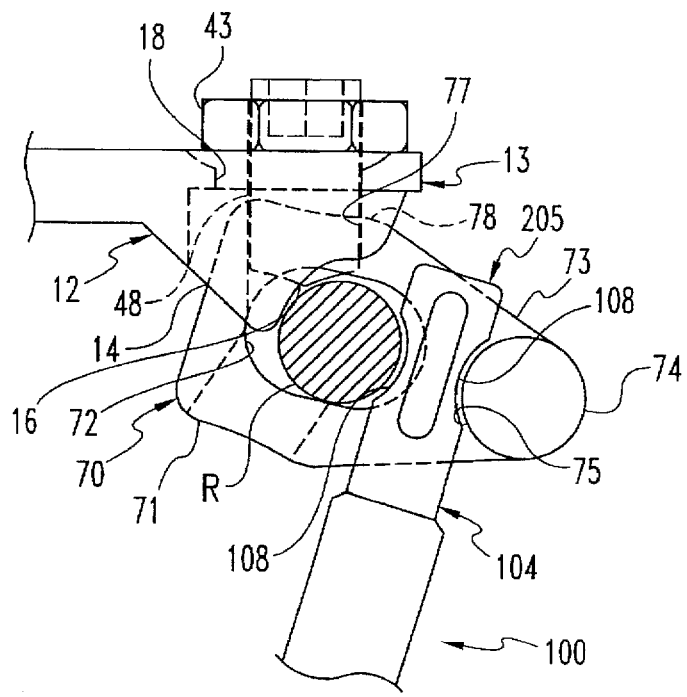
FIG. 11 is an end elevational, partial cross-sectional, view of an alternative top-tightening clamp assembly for use with the spinal hook shown in FIG. 1.

Referring to FIG. 11, this embodiment is illustrated for clamping of spinal hook 100. Specifically, the connection portion 104 of spinal hook 100 is shown disposed between the rod R and the bar 74. The hook 100 is clamped by tightening set screw 40 within threaded bore 77 so that the tip 47 contacts the rod R and presses rod R against the connection portion 104. In turn, the connection portion 104 is pressed against the inward surface 75 of the bar 74. In this way the rod R is clamped between the tip 47 and connection portion 104 and connection portion 104 is clamped between the rod R and the bar 74. The opposing lateral surfaces of the hook 100 are grooves 108 configured to engage the rod R. Preferably, as shown in FIG. 11, the inward surface 75 is compatibly configured with a convex curve toward passage 72. As explained in U.S. Pat. No. 5,246,442, this configuration of opposing lateral surfaces and the compatible inward surface 75 permit orienting the hook 100 so that either side may interchangeably contact rod R. In this variation, the projection 73 accommodates the width of the connection portion 104 alone. Similarly, other types of vertebral fixation elements with a connection portion comparable to connection portion 104 could be clamped in clamp assembly 70. Like the clamp assembly 30 presented in FIGS. 6 and 7, clamp assembly 70 offers a vertebral fixation element clamping means that is initiated and adjusted by way of torquing the set screw 40. Moreover, the clamping means for clamping the transverse connector 10 is independently adjustable by way of threading nut 43 on the threaded proximal end 42 of the set screw 40. Furthermore, both clamping means are adjustable via top-tightening and use the set screw 40, nut 43 and threaded bore 37 as the fastener. Also, the clamping assembly 70 offers an alternative single clamping means for clamping the transverse connector 10, the rod R and the vertebral fixation element between the nut 43 and the bar 74.

Similarly, the clamp assembly 70 can be modified to offer the single clamping means provided by the clamp assemblies in FIGS. 8 and 9. The clamp assembly 70 could also be used with the nut 143 with a spherical bottom surface 144 in conjunction with the sloped recess 119 of FIG. 10 to provide an alternative or additional camming action to the curved shoulder of lower surfaces 16.

It is generally preferred that the projection of the clamp assemblies presented in FIGS. 6–11 terminate in a T-bar so the projection can be easily captured in the slot of the vertebral fixation element during the early stages of assembly. However, it is envisioned that the bar may also be configured to clamp a single post with opposing lateral surfaces configured for engagement in the clamp assembly. A single post connection portion of a vertebral fixation element could also be clamped in the clamp assemblies shown in FIGS. 6–11 by only engaging the inward surface of the T-bar on one side of the projection.

Still other means of independently clamping the vertebral fixation element and the transverse connector exist. For example, the eyebolt of the prior art shown in FIG. 1 could be modified by adding the transverse connector clamping means presented in any of the prior embodiments. The preferred modification is simply a threaded stem attached to the eyebolt which is configured for engagement by a nut 43, or a specially configured nut 143 in conjunction with the sloped recess 119 disclosed in FIG. 10. The transverse connector 10 would be clamped to the longitudinal member by placement so that the thread stem passes through the opening 18, and then threading the nut on the threaded stem so that it presses on upper surface 17.

Prior vertebral fixation element attachment means include attachment to a clamp body which clamps on a longitudinal member, but in which the attachment means operates independent of clamp body clamping on the longitudinal member. Similarly, a clamp body for clamping to a longitudinal member may be integrally formed on the vertebral fixation element. In either case, a stem could be attached to the clamp body which passes through opening 18. A head with a bottom surface for adjustably pressing on the upper surface 17 is attached to a portion of the stem passing through the opening 18. The transverse connector would be clamped to the longitudinal member by placement so that the threaded stem passes through opening 18 and by adjusting the head to press on the upper surface 17.

As shown in FIG. 7, each engagement portion 12 of the transverse connector 10 clamps to the longitudinal member so the axis E is generally perpendicular to the axis along the length of each longitudinal member. Consequently, the clamp assemblies on each longitudinal member are generally aligned as close as possible to each other for optimum clamping of the transverse connector 10. Alternatively, the transverse connector 10 could be bent to accommodate some clamp assembly configurations, but this additional bending complicates the implantation procedure. Another alternative transverse connector could clamp to the longitudinal member at a non-perpendicular angle by forming the engagement portion 12 so that the axis E and an axis along the lower surfaces 16 meet at the desired non-perpendicular angle. However, this approach still restricts the alignment of the clamp assemblies on each longitudinal member to locations dependent on the selected angle. Consequently, the alternative embodiment of a variable angle transverse connector is desirable. For example, FIG. 12 depicts a variable angle transverse connector 400 bridging two generally parallel longitudinal members using the clamp assembly 30 shown in FIGS. 6 and 7.

Figure 12:
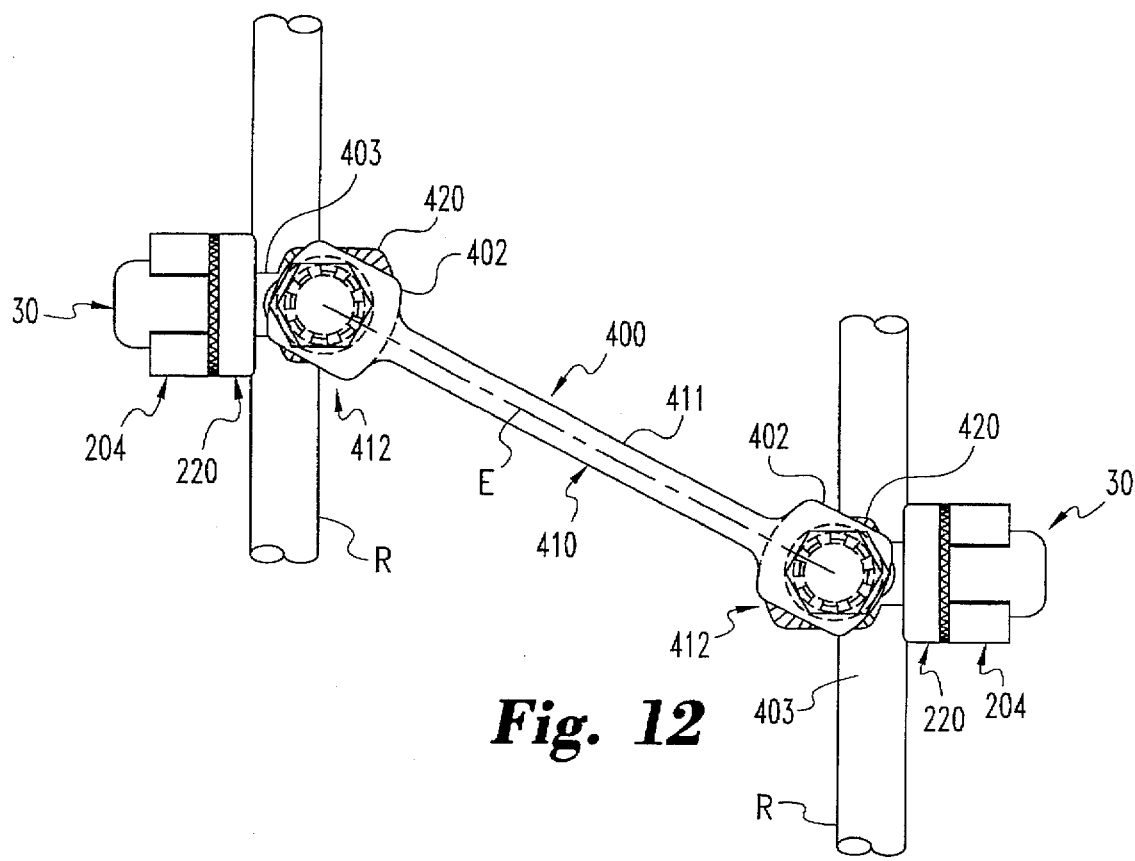
FIG. 12 is a top plan view depicting the clamping of an alternative embodiment of the transverse connector shown in FIGS. 4 and 5 which provides for clamping at a non-normal angle.

Referring to FIG. 12, the variable angle transverse connector 400 has a transverse plate 410 with an elongate body 411. Elongate body 411 has a longitudinal axis E along its length. The variable angle transverse connector 400, having opposing ends, has an engagement portion 412 on each opposing end 403. Alternatively, an engagement portion 412 can be configured at various other locations along the elongate body 411.

Figure 13:
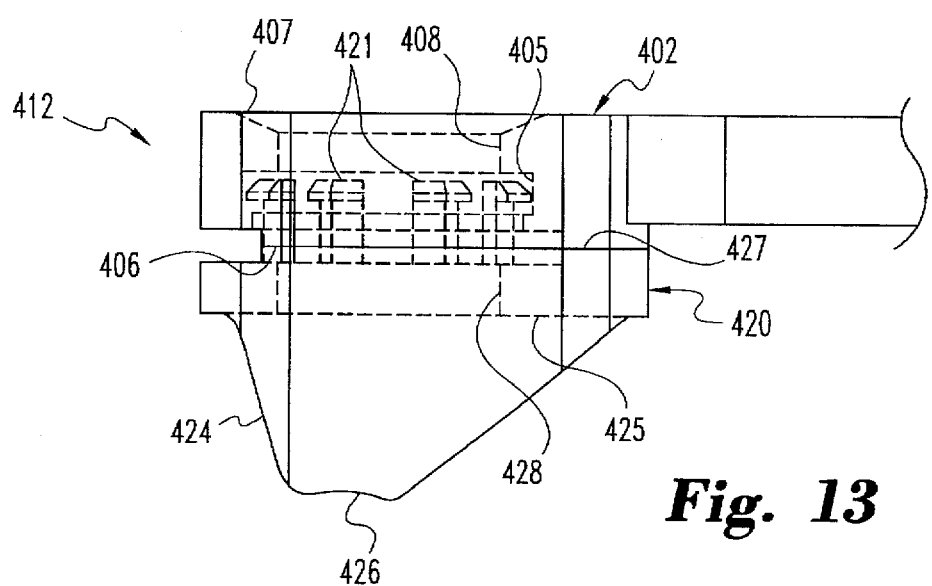
FIG. 13 is a side elevational view, of the alternative embodiment shown in FIG. 12.

Referring to FIG. 13, an engagement portion 412 is configured from a contact portion 402 integrally formed on the transverse plate 410 and an engagement washer 420. Each contact portion 402 of transverse plate 410 has opposing surfaces, an upper surface 407 and a clamping surface 406. The clamping surface 406 and upper surface 407 define a contact portion opening 408 therethrough. The walls of opening 408 define a groove 405 therein.

Figure 14:
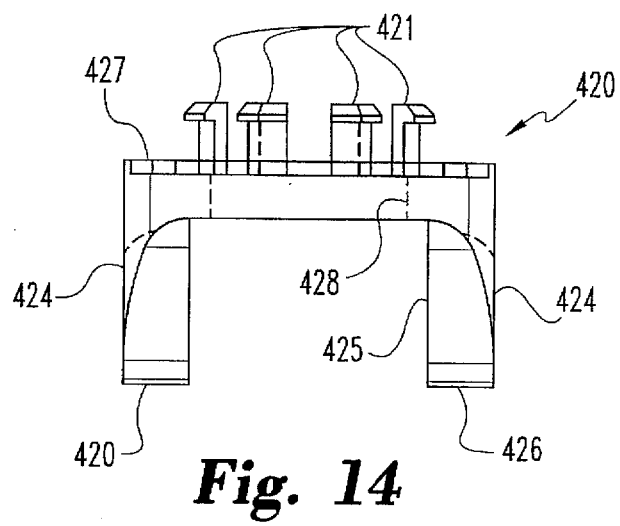
FIG. 14 is an end elevational view of a portion of the alternative embodiment shown in FIG. 12.

Now referring to FIG. 14 which more clearly depicts engagement washer 420. Engagement washer 420 includes a mating surface 427 which defines an engagement washer opening 428 therethrough. Interlocking tabs 421 are integrally formed on engagement washer 420, extending vertically from the mating surface 427. For the present embodiment, eight interlocking tabs 421 are preferred, but more or less are also contemplated. Engagement washer 420 includes a pair of downward legs 424 which are displaced from each other to define a space 425 therebetween. The engagement washer opening 428 intersects space 425. Each downward leg 424 includes a lower surface 426 configured so lower surfaces 426 are coplanar to each other. The lower surfaces 426 are configured to engage a longitudinal member in a manner similar to that described in connection with the above embodiments. For a cylindrical longitudinal member such as rod R, the lower surfaces 426 are formed with a radius groove complimentary to the curvature of rod R.

Referring back to FIG. 13, interlocking tabs 421 are configured to engage groove 405 so that contact portion opening 428 aligns with engagement washer opening 408 and engagement washer 420 is loosely coupled to the contact portion 402. As a consequence, openings 428 and 408 intersect the space 425 when aligned. The interlocking tabs 421 are configured so that the engagement washer 420 rotates freely about an axis through the aligned openings 408 and 428, when the interlocking tabs 421 are received in the groove 405. The interlocking tabs 421 and groove 405 can be configured so the engagement washer 420 is press fitted onto the contact portion 402. Alternatively, a staking tool can be used to depress a portion of the interlocking tabs 421 into groove 405. Preferably the coupling of the engagement washer 420 to the contact portion 402 is done prior to implanting the transverse connector 400 within the patient, or engaging it onto a longitudinal member.

Like the transverse connector assemblies depicted in FIGS. 6–11, the engagement washer 420 is configured so that the downward legs 424 straddle at least a portion of a clamp assembly when the lower surfaces 426 engage a longitudinal member extending through the clamp assembly passage. The space 425, engagement washer opening 428 and contact portion opening 408 are configured to receive at least a portion of the clamp assembly when the lower surfaces 416 engage a longitudinal member extending through the clamp assembly passage and interlocking tabs 421 are received in groove 405.

Figure 15:
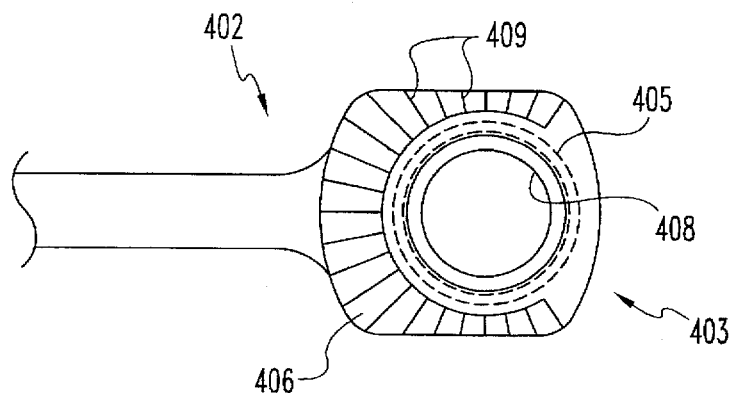
FIG. 15 is top plan view of the portion of the alternative embodiment shown in FIG. 13.
Figure 16:
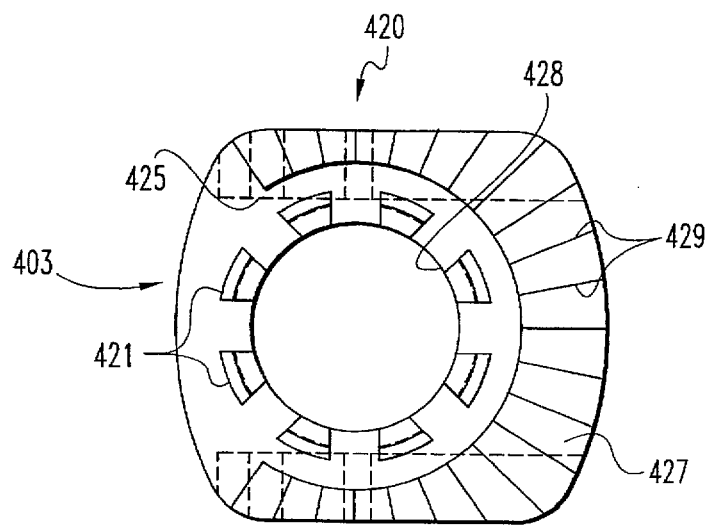
FIG. 16 is a bottom plan view of a portion of the alternative embodiment shown in FIG. 12.

Preferably, the variable angle transverse connector 400 employs a radial spline structure similar to the variable angle bone screw 200 and clamp assembly washer 220 depicted in FIGS. 2 and 3, respectively, to provide rigid variable angle clamping capability. Specifically, FIG. 15 shows a top plan view of engagement washer 420 prior to connection to the transverse connector plate 410 to clearly depict a plurality of radial splines 429 on the mating surface 427. Radial splines 429 are configured comparably with the radial splines 409 shown on clamping surface 406 as depicted in the bottom plan view offered by FIG. 16 of contact portion 402. The radial splines 429 of the engagement washer 420 and the radial splines 409 of the contact portion 402 are configured to interdigitate when the mating surface 427 and the clamping surface 406 meet.

As depicted in FIG. 12, one improved system using variable angle transverse connector 400 employs clamp assembly 30 of FIGS. 6 and 7 including the fastener offered by set screw 40, threaded bore 37 and nut 43. First, with the engagement washer 420 loosely coupled to the transverse connector plate 410, the engagement washer 420 is oriented so that the downward legs 424 straddle the clamp assembly and the lower surfaces 426 engage the longitudinal member received in the passage of the clamp assembly. A stem passes through engagement washer opening 428 and contact portion opening 408. A head is attached to a portion of the stem passing through the opening 428 and 408. This head has a bottom surface with a means for adjustably pressing the bottom surface against the upper surface 407 of contact portion 402.

Prior to contact between the bottom surface of the head and the upper surface 407, the engagement washer 420 is still free to rotate. However, as the head is adjusted to press on the upper surface 407, the clamping surface 406 of the contact portion 402 presses against the mating surface 427 of the engagement washer 420, clamping the contact portion 402 between the head and the engagement washer 420. Contact between clamping surface 406 and mating surface 427 occurs because the height of the interlocking tabs 421 from the mating surface 407 is less than the distance from the top of the groove 405 to the clamping surface 406. As the clamping surface 406 presses against mating surface 427 of the engagement washer 420, the lower surfaces 426 press against the longitudinal member clamping the engagement washer 420 between the contact portion 402 and the longitudinal member. Consequently, contact portion 402 and engagement washer 420 of the engagement portion 412 are clamped together and engagement portion 412 of variable angle transverse connector 400 is clamped between the head and the longitudinal member.

Moreover, as the clamping surface 406 of the contact portion 402 and the mating sur#ace 427 of the engagement washer 420 are clamped together, the splines 409 and splines 429 interdigitate. Interdigitation of splines 429 and splines 409 facilitate rigid fixation of the engagement washer 420 to the longitudinal member at the desired angle between the axis E and the axis along the length of the longitudinal member as shown in FIG. 12. Similarly, the variable angle transverse connector 400 could be used with other various fasteners and associated clamping means previously discussed herein.

As an alternative embodiment, it should be noted that the engagement washer 420 can be adapted for use with existing transverse connection devices. For example, the CROSSLINK® system illustrated in the "TSRH® Surgical Manual" could be used with an engagement washer to facilitate clamping with the same clamp assembly as the vertebral fixation element and at the same location along the longitudinal member. In this embodiment, the engagement washers are not initially connected to the transverse connector. Instead, an engagement washer is placed on a clamp assembly and the existing transverse member is clamped to the engagement washer by way of an eyebolt or other compatible clamping means. In particular, for use with a CROSSLINK®, the engagement washer does not need interlocking tabs 421 because no grooves exist to loosely couple the engagement washer 420 to the CROSSLINK®. However, the advantage of clamping using an existing transverse connector at the same site along the longitudinal member as a vertebral fixation element is realized. Similarly, the engagement washer can be modified for use with other existing transverse connectors.

Figure 17:
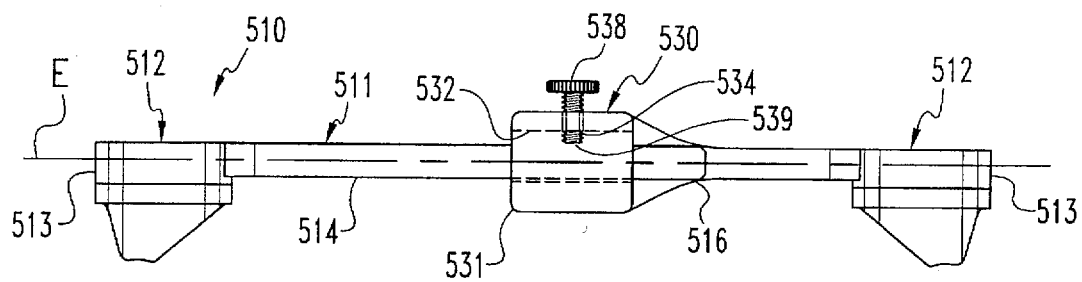
FIG. 17 is a side elevational view of an alternative embodiment of the transverse connector having an adjustable elongate body length.

In another preferred embodiment of the present invention, the transverse connector has an elongate body with an adjustable length. Referring to FIG. 17, an adjustable length elongate body 511 with a longitudinal axis E of transverse connector 510 is illustrated. Elongate body 511 has a first arm 514 and a second arm 516 connected by a joining clamp 530. Each arm 514 and 516 has an engagement portion 512 formed on an end 513. When the first arm 514 and second arm 516 are connected by the joining clamp 530, the engagement portions 512 are on opposite ends 513 of the elongate body 511 along axis E. Besides engagement portion 512, another engagement portion configuration or a contact portion may be alternatively employed as described in earlier embodiments.

Figure 18:
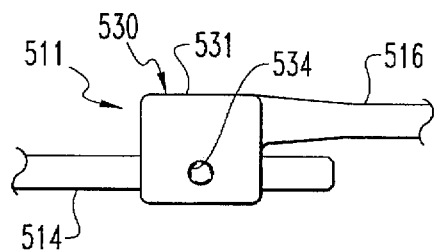
FIG. 18 is a top plan view of a portion of the alternative embodiment shown in FIG. 17.

The joining clamp 530 has a joining clamp body 531 integrally formed on second arm 512. The joining clamp body 531 defines a passage 532 therein. The passage 532 is approximately parallel to the longitudinal axis E and is configured to receive first arm 514. In addition, the joining clamp body 531 defines a threaded bore 534 intersecting passage 532. Threaded bore 534 is configured to receive a set screw 538. Set screw 538 has a tip 539 configured to bear against the first arm 514. FIG. 18 shows a partial top plan view of the elongate body assembly shown in FIG. 17 with the set screw 538 removed for clarity.

Referring generally to FIGS. 17 and 18, the operation of the device is now discussed. The elongate body is assembled by placing the first arm 514 in the passage 532 and moving the first arm 514 within the passage 532 a distance corresponding to the desired overall length along axis E. The elongate body is shortened by increasing the length of the first arm 514 engaging the passage 532. The elongate body is lengthened by decreasing the length of the first arm 514 engaging the passage 532. The set screw 538 is then threaded in the threaded bore 534 until the tip 539 of set screw 538 bears against the first arm 514. As a result, the first arm 514 is clamped between the tip 539 and the passage 532 to fix the desired length of the elongate body 511. It can be appreciated that a portion of the first arm 514 must remain clamped between the tip 539 and passage 532 for the first arm 514 and second arm 516 to remain joined.

Figure 19:
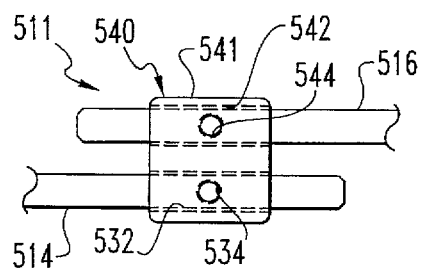
FIG. 19 is a top plan view of an alternative joining clamp to adjust elongate body length of a transverse connector.

Now referring to FIG. 19, a variation of the embodiment shown in FIGS. 17 and 18 is depicted. In this variation, the joining clamp body 541 is not integrally connected to the second arm 516, but instead is configured to clamp the second arm 516 approximately parallel to the first arm 514 in a like manner. Specifically, this embodiment includes a joining clamp 540 with a second passage 542 defined by joining clamp body 541. This second passage 542 is approximately parallel to a first passage 532. The second passage 542 is intersected by a threaded bore 544. Similarly, first passage 532 is intersected by a threaded bore 534. Threaded bores 534 and 544 are configured for engagement by a set screw like the set screw 538 employed in the clamp assembly 530 of the embodiment shown in FIG. 17.

The length of the elongate body 511 is set by adjusting the first arm 514 in the manner described for the embodiment shown in FIGS. 17 and 18. Similarly, the length of the elongate body 511 may also be adjusted by selecting the desired length of second arm 516 to engage the second passage 542 and to clamp the second arm 516 between a set screw 538 and passage 542.

Figure 20:
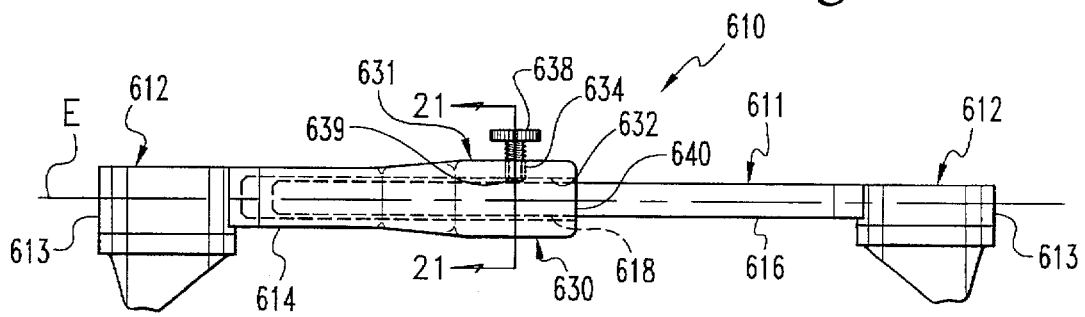
FIG. 20 is a side elevational view of am alternative embodiment of the transverse connector having an adjustable elongate body length.

Referring to FIG. 20, another embodiment of a transverse connector 610 with an adjustable length elongate body 611 having a longitudinal axis E is illustrated. Elongate body 611 has a first arm 614 and a second arm 616 connected by a joining clamp 630. Each arm 614 and 616 has an engagement portion 612 formed on an end 613. When the first arm 614 and second arm 616 are joined by the joining clamp 630, the engagement portions 612 are on opposite ends 613 of the elongate body 611 along axis E. Besides engagement portion 612, an engagement portion configuration or a contact portion may be alternatively employed as described in earlier embodiments.

Figure 21:
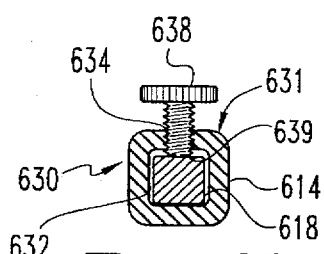
FIG. 21 is a cross-sectional view of the embodiment shown in FIG. 20.

The joining clamp 630 has a joining clamp body 631 integrally formed as part of first arm 614 including a joining end 640 opposite end 613 of the first arm 614. The joining clamp body 631 defines a nesting passage 632 therein. The nesting passage 632 is approximately parallel to the longitudinal axis E and is configured to receive a nesting portion 618 of second arm 616. Nesting portion 618 is generally opposite the end 613 of second arm 616. In addition, the joining clamp body 631 defines a threaded bore 634 intersecting nesting passage 632. Threaded bore 634 is configured to receive a set screw 638. Set screw 638 has a tip 639 configured to bear against the second arm 616. FIG. 21 shows a cross-sectional view of the joining clamp 630.

Figure 22:
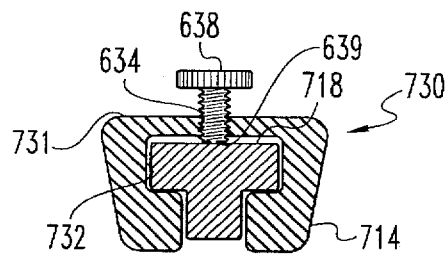
FIG. 22 is a cross-sectional view of an alternative embodiment of the adjustable elongate body shown in FIGS. 20 and 21.

FIG. 22 shows a cross-sectional view of an alternatively shaped nesting passage 732 in a joining clamp body 731 of a joining clamp 730. Similarly, the nesting portion 718 is correspondingly shaped to engage the passage 732. The set screw 638 with tip 639 and threaded bore 639 are the same as those shown in FIG. 21. A variety of nesting passage shapes and correspondingly shaped nesting portions could be employed as would occur to one of ordinary skill in the art.

Referring generally to FIGS. 20 and 21, the operation of the adjustable length elongate body 611 is now discussed. The elongate body is assembled by placing the nesting portion 618 of second arm 616 within nesting passage 632 an amount corresponding to the desired overall length of elongate body 611 along axis E. The elongate body is shortened by increasing the length of the nesting portion 618 within the nesting passage 632. The elongate body is lengthened by decreasing the length of the nesting portion 618 within the nesting passage 632. The set screw 638 is then threaded in the threaded bore 634 until the tip 639 of set screw 638 bears against the nesting portion 618 of second arm 616. As a result, the second arm 616 is clamped between the tip 639 and the nesting passage 632 to fix the desired length of the elongate body 611. It can be appreciated that a portion of the nesting portion 618 of the second arm 616 must remain clamped between the tip 639 and passage 632 for the first arm 614 and second arm 616 to remain joined.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A top-loading transverse connector for bridging between two longitudinal members extending adjacent the spine of a patient, each carrying a clamp assembly thereon for attaching a vertebral engaging element to the longitudinal member, comprising:

an elongate body defining a longitudinal axis and having a first end opposite a second end, the length of said elongate body being sized to span the distance between the two longitudinal members, each of said first end and said second end including an engagement portion having:

a pair of downward legs displaced from each other to define a space therebetween;

each of said legs including a lower surface configured to engage the longitudinal member, said lower surface of each of said legs being coplanar to each other;

an upper surface opposite said lower surface and defining an opening therethrough, said opening intersecting said space defined between said pair of legs; whereby said space and said opening are configured to receive the clamp assembly therein when the clamp assembly is carried on the longitudinal member and when said elongate body is disposed between said two longitudinal members and over the clamp assembly, wherein said elongate body includes:

a first arm with said first end:

a second arm with said second end:

a joining clamp connecting said first arm to said second arm, said joining clamp being located between said first end and said second end and being adjustable to fix the length of said elongate body between said first end and said second end, said joining clamp including a joining clamp body defining:

a first passage for receiving said first arm, said first passage being approximately parallel to the longitudinal axis of said elongate body;

a second passage for receiving said second arm, said second passage being approximately parallel to said first passage;

a first threaded bore intersecting said first passage:

a second threaded bore intersecting said second passage;

a first set screw configured to engage said first threaded bore, said first set screw having a first tip configured to bear against said first arm:

a second set screw configured to engage said second threaded bore, said second set screw having a second tip configured to bear against said second arm, and whereby said first arm is received in said first passage and said second arm is received in said second passage, said first and second arms are selectively positioned relative to each other to establish length of said elongate body, said first arm is clamped in said first passage by threading said first set screw in said first threaded bore so said first tip bears against said first arm, and said second arm is clamped in said second passage by threading said second set screw in said second threaded bore so that said second tip bears against said second arm.

2. The transverse connector of claim 1 wherein each said lower surface defines a cam surface configured to displace the longitudinal member when said elongate body is clamped to the longitudinal member.

3. The transverse connector of claim 1 wherein said transverse connector is symmetric about a plane formed perpendicular to said longitudinal axis and between said first end and said second end.

4. The transverse connector of claim 1 wherein said transverse connector is symmetric about a plane coincident with said longitudinal axis and between said downward legs of each engagement portion.

5. A spinal fixation system, comprising:

a) a first longitudinal member configured for placement adjacent the spine of a patient;

b) a vertebral fixation element including:

a vertebra engaging portion;

a connection portion;

c) a first clamp assembly including:

a first clamp body defining a passage therethrough configured to receive said first longitudinal member;

a first means for attaching said connection portion of said vertebral fixation element to said first clamp body;

d) a transverse connector including:

an elongate body defining a longitudinal axis along its length;

a first engagement portion formed on a portion of said elongate body having a first surface configured to engage said first longitudinal member and an upper surface defining an engagement portion opening therethrough; and e) a first fastener attaching said first clamp body to said first engagement portion of said transverse connector with said first surface engaging said longitudinal member, said first fastener extending through said engagement portion opening, said first fastener including:

a threaded stem, having opposite ends, one end being attached to said first clamp body and said opposing end passing through said engagement portion opening;

a nut configured for threading on said threaded stem, said nut having a bottom surface for engaging said upper surface of said first engagement portion when said stem passes through said engagement portion opening.

6. The spinal fixation system of claim 5 wherein said first surface defines a cam surface configured to displace said first longitudinal member in a direction parallel to said longitudinal axis of said transverse connector when said elongate body is attached to said first longitudinal member by said first fastener.

7. The spinal fixation system of claim 5 wherein said elongate body includes a first end opposing a second end, said first engagement portion is integrally configured on said first end, and further comprising:

a second engagement portion integrally configured on said second end of said transverse connector;

a second longitudinal member generally parallel to said first longitudinal member;

a second clamp assembly including a second clamp body defining a passage therethrough configured to receive said second longitudinal member;

a second fastener attaching said second engagement portion to said second clamp body.

8. The spinal fixation system of claim 5 wherein:

said first longitudinal member is a rod;

said passage in said clamp assembly is an elongate bore, said bore having a length along its longitudinal axis greater than the diameter of said rod so that said rod can at least initially slide within said bore;

said first clamp body includes a projection extending generally perpendicular to the longitudinal axis defined by said first longitudinal member received in said passage, said projection terminating in a T-bar having an inward surface directed toward said passage;

said connection portion includes a pair of posts defining a slot therebetween configured for receiving said projection.

9. The spinal fixation system of claim 8 wherein:

at least one of said opposing lateral surfaces, of each of said pair of posts includes a plurality of splines; and said first clamp assembly includes a washer having a clamping surface configured to engage said first longitudinal member, and an opposite mating surface which includes a plurality of radial splines adapted for interdigitating engagement with the radial splines of said pair of posts, said washer further defining:
  an opening therethrough configured to permit insertion of said washer over said T-bar; and
  means for slidably engaging said washer to said body adjacent said passage,
wherein said washer is disposed between said vertebral fixation element connection portion and said first longitudinal member and is clamped therebetween by said first clamping means.

10. The spinal fixation system of claim 5 wherein:
said engagement portion includes a pair of downward legs displaced from each other to define a space therebetween, said space intersecting said first engagement portion opening, said space being sufficient to straddle said first clamp body;
said first surface includes a lower surface on each of said pair of downward legs, said lower surface on each of said legs being coplanar to each other.

11. The spinal fixation system of claim 5 wherein:
said engagement portion includes a contact portion with said upper surface, said contact portion including a clamping surface opposite said upper surface, said upper surface and said clamping surface defining a contact portion opening therethrough;
an engagement washer having:
  a pair of downward legs displaced from each other to define a space therebetween, said space being sufficient to straddle said first clamp body;
  a mating surface configured to engage said clamping surface, said mating surface being opposite said first surface and defining an engagement washer opening therethrough, said engagement washer opening intersecting said space defined between said pair of legs;
said engagement washer opening configured to align with said contact portion opening to form said engagement portion opening when said mating surface engages said clamping surface;
said first surface includes a lower surface on each of said pair of downward legs, said lower surface on each of said legs being coplanar to each other,
whereby said space and said engagement portion opening are configured to receive the clamp assembly therein when the clamp assembly is carried on said first longitudinal member.

12. The spinal fixation system of claim 11 wherein:
said contact portion opening includes a wall defining a groove therein;
said engagement washer includes a plurality of interlocking tabs extending vertically from said mating surface for engaging said groove to align said contact portion opening with said engagement washer opening,
whereby said engagement washer is coupled to said contact portion by engagement of said interlocking tabs in said groove on each opposing end of said elongate body.

13. A top-loading variable angle transverse connector for bridging between two longitudinal members extending adjacent the spine of a patient, each carrying a clamp assembly thereon for attaching an element to the longitudinal member, comprising:

an elongate body defining a longitudinal axis and having a first end opposite a second end, the length of said elongate body being sized to span the distance between the two longitudinal members, each of said first end and said second end including an engagement portion having:
  a contact portion integrally formed on each opposing end of said elongate body having:
    an upper surface;
    a clamping surface opposing said upper surface;
    said upper surface and said clamping surface defining a contact portion opening therethrough;
    wall of said contact portion opening defining a groove therein; and an engagement washer having:
    a pair of downward legs displaced from each other to define a space therebetween;
    each of said legs including a lower surface configured to engage the longitudinal member, said lower surface of each of said legs being generally coplanar;
    a mating surface opposite said lower surfaces and configured to engage said clamping surface and defining an engagement washer opening therethrough, said engagement washer opening intersecting said space defined between said pair of legs;
    a plurality of interlocking tabs extending vertically from said mating surface for engaging said groove and aligning said contact portion opening with said engagement washer opening; and
  wherein said clamping surface and said mating surface include a plurality of radial splines adapted for interdigitating engagement when said clamping surface and said mating surface are clamped together,
  whereby said space, said contact portion opening and said engagement washer opening are configured to receive the clamp assembly therein when the clamp assembly is carried on the longitudinal member, said elongate body is disposed between two longitudinal members and said engagement washer is coupled to said contact portion by engagement of said interlocking tabs in said groove on each opposing end of said elongate body.

14. The variable angle transverse connector of claim 13 wherein said transverse connector is symmetric about a plane formed perpendicular to said longitudinal axis and between said first end and said second end.

15. The variable angle transverse connector of claim 13 wherein said transverse connector is symmetric about a plane coincident with said longitudinal axis and between said downward legs of each engagement portion.

16. The variable angle transverse connector of claim 13 wherein said elongate body includes:
a first arm with said first end;
a second arm with said second end;
a joining clamp connecting said first arm to said second arm so that said first arm and said second arm are generally parallel to said longitudinal axis, said joining clamp being located between said first end and said second end, said joining clamp being adjustable to fix the length of said elongate body between said first end and said second end.

17. The variable angle transverse connector of claim 16 wherein said joining clamp includes:
a joining clamp body defining:
  a first passage for receiving said first arm, said first passage being approximately parallel to the longitudinal axis of said elongate body;

a first threaded bore intersecting said first passage;
first set screw configured to engage said first threaded bore, said first set screw having a first tip configured to bear against said first arm;
an attachment of said joining clamp body to said second arm;
whereby said first arm is received in said first passage and the length of said elongate body is established by the position of said first arm in said first passage and said first arm is clamped in said first passage by threading said first set screw in said first threaded bore so said first tip bears against said first arm.

18. The variable angle transverse connector of claim 17 wherein said joining clamp attachment to said second arm includes:
said joining clamp defining:
a second passage for receiving said second arm, said second passage being approximately parallel to said first passage;
a second threaded bore intersecting said second passage;
a second set screw configured to engage said second threaded bore, said second set screw having a second tip configured to bear against said second arm when said second set screw engages said second threaded bore,
whereby the length of said elongate body is determined by positioning said second arm in said second passage and attaching said second arm in said second passage by threading said second set screw in said second threaded bore until said second tip bears against said second arm.

19. The variable angle transverse connector of claim 16 wherein:
said joining clamp includes a joining clamp body formed on said first arm on an end opposite said first end of said elongate body, said joining clamp body defining:
a nesting passage approximately parallel to the longitudinal axis of said elongate body;
a threaded bore therethrough, said threaded bore intersecting said nesting passage;
said second arm has a nesting portion, said nesting portion being configured to nest within said nesting passage;
said joining clamp includes a set screw configured to engage said threaded bore, said set screw having a tip configured to engage said second arm nesting within said nesting passage,
whereby said second arm is received in said nesting passage and the length of said elongate body is established by the position of said second arm in said nesting passage and said first arm and said second arm are clamped together by receiving said nesting portion in said nesting passage and threading said set screw in said threaded bore so said first tip bears against said second arm.

20. A spinal fixation system, comprising:
a) a first longitudinal member configured for placement adjacent the spine of a patient;
b) a vertebral fixation element including:
a vertebra engaging portion;
a connection portion;
c) a first clamp assembly including:
a first clamp body defining a passage therethrough configured to receive said first longitudinal member;
a first means for attaching said connection portion of said vertebral fixation element to said first clamp body;

d) a transverse connector including:
an elongate body defining a longitudinal axis along its length;
a first engagement portion formed on a portion of said elongate body having a first surface configured to engage said first longitudinal member and an upper surface defining an engagement portion opening therethrough; and
e) a first fastener attaching said first clamp body to said first engagement portion of said transverse connector with said first surface engaging said longitudinal member, said first fastener extending through said engagement portion opening, and
wherein said first clamp body defines a threaded bore therein and said first fastener includes:
a stem threaded to engage said threaded bore, said stem being sized to pass through said engagement portion opening;
a head integrally formed on an end of said stem having a bottom surface for engaging said upper surface of said first engagement portion when said stem passes through said engagement portion opening and is threaded into said threaded bore.

21. The spinal fixation system of claim 20 wherein:
said engagement portion includes a pair of downward legs displaced from each other to define a space therebetween, said space intersecting said first engagement portion opening, said space being sufficient to straddle said first clamp body;
said first surface includes a lower surface on each of said pair of downward legs, said lower surface on each of said legs being coplanar to each other.

22. The spinal fixation system of claim 20 wherein: said engagement portion includes a contact portion with said upper surface, said contact portion including a clamping surface opposite said upper surface, said upper surface and said clamping surface defining a contact portion opening therethrough; an engagement washer having;
a pair of downward legs displaced from each other to define a space therebetween, said space being sufficient to straddle said first clamp body;
a mating surface configured to engage said clamping surface, said mating surface being opposite said first surface and defining an engagement washer opening therethrough, said engagement washer opening intersecting said space defined between said pair of legs;
said engagement washer opening configured to align with said contact portion opening to form said engagement portion opening when said mating surface engages said clamping surface;
said first surface includes a lower surface on each of said pair of downward legs, said lower surface on each of said legs being coplanar to each other,
whereby said space and said engagement portion opening are configured to receive the clamp assembly therein when the clamp assembly is carried on the longitudinal member.

23. The spinal fixation system of claim 20 wherein said first surface defines a cam surface configured to displace said first longitudinal member in a direction parallel to said longitudinal axis of said transverse connector when said elongate body is attached to said first longitudinal member by said first fastener.

24. The spinal fixation system of claim 20 wherein said elongate body includes a first end opposing a second end, said first engagement portion is integrally configured on said first end, and further comprising:

a second engagement portion integrally configured on said second end of said transverse connector;

a second longitudinal member generally parallel to said first longitudinal member;

a second clamp assembly including a second clamp body defining a passage therethrough configured to receive said second longitudinal member;

a second fastener attaching said second engagement portion to said second clamp body.

25. The spinal fixation system of claim 20 wherein:

said first longitudinal member is a rod;

said passage in said clamp assembly is an elongate bore, said bore having a length along its longitudinal axis greater than the diameter of said rod so that said rod can at least initially slide within said bore;

said first clamp body includes a projection extending generally perpendicular to the longitudinal axis defined by said first longitudinal member received in said passage, said projection terminating in a T-bar having an inward surface directed toward said passage;

said connection portion includes a pair of posts defining a slot therebetween configured for receiving said projection.

26. The spinal fixation system of claim 25 wherein:

at least one of said opposing lateral surfaces, of each of said pair of posts includes a plurality of splines; and said first clamp assembly includes a washer having a clamping surface configured to engage said first longitudinal member, and an opposite mating surface which includes a plurality of radial splines adapted for interdigitating engagement with the radial splines of said pair of posts, said washer further defining;

an opening therethrough configured to permit insertion of said washer over said T-bar; and means for slidably engaging said washer to said body adjacent said passage, wherein said washer is disposed between said vertebral fixation element connection portion and said first longitudinal member and is clamped therebetween by said first clamping means.

\* \* \* \* \*